US006896692B2

(12) United States Patent
Ginn et al.

(10) Patent No.: US 6,896,692 B2
(45) Date of Patent: May 24, 2005

(54) PLUG WITH COLLET AND APPARATUS AND METHOD FOR DELIVERING SUCH PLUGS

(75) Inventors: Richard S. Ginn, San Jose, CA (US); Daniel T. Wallace, Redwood City, CA (US); Robert C. LaDuca, Davenport, CA (US)

(73) Assignee: Ensure Medical, Inc., Sunnyvale, CA (US)

( * ) Notice: Subject to any disclaimer, the term of this patent is extended or adjusted under 35 U.S.C. 154(b) by 482 days.

(21) Appl. No.: 10/142,735

(22) Filed: May 10, 2002

(65) Prior Publication Data

US 2003/0032858 A1 Feb. 13, 2003

Related U.S. Application Data

(63) Continuation-in-part of application No. 09/866,548, filed on May 25, 2001, now Pat. No. 6,663,655, which is a continuation-in-part of application No. 09/738,431, filed on Dec. 14, 2000.

(51) Int. Cl.[7] .................................................. A61B 17/08

(52) U.S. Cl. ........................................................ 606/213

(58) Field of Search .................................. 606/213, 157, 606/151, 108, 200, 217, 232, 95; 600/585; 623/1.1

(56) References Cited

U.S. PATENT DOCUMENTS

| | | | | |
|---|---|---|---|---|
| 4,890,612 A | | 1/1990 | Kensey | |
| 5,292,332 A | * | 3/1994 | Lee | 606/213 |
| 5,690,674 A | | 11/1997 | Diaz | |
| 6,086,608 A | | 7/2000 | Ek et al. | |

* cited by examiner

*Primary Examiner*—Julian W. Woo
(74) *Attorney, Agent, or Firm*—Orrick, Herrington & Sutcliffe LLP

(57) ABSTRACT

An apparatus for sealing a passage through tissue includes a plug including external threads, a lumen extending between its proximal and distal ends, and an annular collet slidably disposed within the lumen. The plug is carried on a distal end of a handle device that includes an inner member with a distal end that is slidable axially within the lumen of the body for moving the collet into a reduced cross-sectional region of the lumen, thereby compressing the collet to seal the lumen, and for deploying the plug from the handle device. During use, the plug is threaded into a passage through tissue over a guide wire. Once a desired location is reached, the plug is deployed from the handle device, thereby compressing the collet and sealing the lumen. The guide wire and handle device are removed, leaving the plug to seal the passage.

25 Claims, 12 Drawing Sheets

14 12 60 21 77a 20 76 89 80 70 23 61 88 28 22 63 62 64 65 77 86 89 26 86 84 74

PLUG WITH COLLET AND APPARATUS AND METHOD FOR DELIVERING SUCH PLUGS

CROSS-REFERENCE TO RELATED APPLICATIONS

This application is a continuation-in-part of application Ser. No. 09/866,548, filed May 25, 2001 now U.S. Pat. No. 6,663,655, which is a continuation-in-part of application Ser. No. 09/738,431, filed Dec. 14, 2000, the disclosures of which are expressly incorporated herein by reference.

FIELD OF THE INVENTION

The present invention relates generally to apparatus and methods for sealing or closing passages through tissue, and more particularly to devices for sealing punctures or other openings communicating with body lumens, such as blood vessels, and to apparatus and methods for delivering such devices.

BACKGROUND

Catheterization and interventional procedures, such as angioplasty or stenting, generally are performed by inserting a hollow needle through a patient's skin and any intervening tissue into the vascular system. A guide wire may then be passed through the needle lumen into the patient's blood vessel accessed by the needle. The needle may be removed, and an introducer sheath may be advanced over the guide wire into the vessel, e.g., in conjunction with or subsequent to a dilator. A catheter or other device may then be advanced through a lumen of the introducer sheath and over the guide wire into a position for performing a medical procedure. Thus, the introducer sheath may facilitate introducing various devices into the vessel, while minimizing trauma to the vessel wall and/or minimizing blood loss during a procedure.

Upon completing the procedure, the devices and introducer sheath may be removed, leaving a puncture site in the vessel wall. External pressure may be applied to the puncture site until clotting and wound sealing occur. This procedure, however, may be time consuming and expensive, requiring as much as an hour of a physician's or nurse's time. It is also uncomfortable for the patient, and requires that the patient remain immobilized in the operating room, catheter lab, or holding area. In addition, a risk of hematoma exists from bleeding before hemostasis occurs.

Various apparatus have been suggested for percutaneously sealing a vascular puncture by occluding the puncture site. For example, U.S. Pat. Nos. 5,192,302 and 5,222,974, issued to Kensey et al., describe the use of a biodegradable plug that may be delivered through an introducer sheath into a puncture site. When deployed, the plug may seal the vessel and provide hemostasis. Such devices, however, may be difficult to position properly with respect to the vessel, which may be particularly significant since it is generally undesirable to expose the plug material, e.g., collagen, within the bloodstream, where it may float downstream and risk causing an embolism.

Another technique has been suggested that involves percutaneously suturing the puncture site, such as that disclosed in U.S. Pat. No. 5,304,184, issued to Hathaway et al. Percutaneous suturing devices, however, may require significant skill by the user, and may be mechanically complex and expensive to manufacture.

Staples and surgical clips have also been suggested for closing wounds or other openings in tissue. For example, U.S. Pat. Nos. 5,007,921 and 5,026,390, issued to Brown, disclose staples that may be used to close a wound or incision. In one embodiment, an "S"-shaped staple is disclosed that includes barbs that may be engaged into tissue on either side of the wound. In another embodiment, a ring-shaped staple is disclosed that includes barbs that project from the ring. These staples, however, have a large cross-sectional profile and therefore may not be easy to deliver through a percutaneous site to close an opening in a vessel wall.

In addition, skin seals have been proposed that may be threaded into an opening in skin. For example, U.S. Pat. No. 5,645,565, issued to Rudd et al., discloses a surgical plug that may be screwed into a puncture to seal the puncture. The surgical plug includes an enlarged cap and a threaded shaft that extends from the cap. During an endoscopic procedure, the plug may be threaded into an opening through skin until the cap engages the surface of the skin. The plug is intended to seal the opening communicating with a body cavity to prevent insufflation fluid from leaking from the cavity. Such plugs, however, may only be used at the surface of the skin, and may not be introduced through tissue, for example, to seal an opening in the wall of a blood vessel or other subcutaneous region.

Accordingly, devices for sealing punctures or other passages through tissue, e.g., an opening into a blood vessel, would be considered useful.

SUMMARY OF THE INVENTION

The present invention is directed to apparatus and methods for sealing or closing passages through tissue, such as punctures communicating with blood vessels or other body lumens.

In accordance with one aspect of the present invention, a device for sealing a passage through tissue is provided that includes a body or plug member including a proximal end and a distal end. The body generally includes a lumen extending between the proximal and distal ends, the lumen including a reduced cross-sectional region, e.g., a tapered distal region. The body may include elements, e.g., a helical thread pattern, flutes, ribs, and/or ridges, on an outer surface thereof that extend at least partially between the proximal and distal ends. Such elements may facilitate advancing the body into a passage through tissue and/or sealing the passage. Alternatively, the outer surface may be substantially smooth.

A sealing member, e.g., having a generally annular shape, is slidably disposed within the lumen of the body that includes a lumen extending between proximal and distal ends thereof, and a plurality of shoulders disposed about the lumen of the sealing member. The shoulders may be deflectable towards one another when the sealing member is moved at least partially into the reduced cross-sectional region, thereby at least partially sealing the lumen of the sealing member and/or the lumen of the body.

The body and/or the sealing member may be formed from biocompatible and/or bioabsorbable material. Preferably, both the body and the sealing member are bioabsorbable, thereby providing a plug member that may be delivered into a body passage to substantially seal and/or close the passage, the plug member remaining within the passage until it is absorbed by surrounding tissue.

In accordance with another aspect of the present invention, an apparatus is provided for sealing a passage through tissue, e.g., to deliver a plug member. The apparatus may include a plug member, such as that described above, e.g., including a body having a lumen extending between proximal and distal ends thereof. The lumen may include a reduced cross-sectional region, e.g., a tapered distal region. A sealing member may be slidably disposed within the lumen of the body that is compressible when directed into the reduced cross-sectional region for at least partially sealing the lumen of the sealing member and/or the lumen of the body. For example, the sealing member may include a plurality of shoulders disposed about a lumen of the sealing member that are deflectable towards one another.

In addition, the apparatus may include a handle device including an elongate outer member and an elongate inner member having proximal and distal ends defining a longitudinal axis therebetween. The distal end of the outer member may be detachably coupled to the proximal end of the body. In addition or alternatively, the distal end of the inner member may be slidable axially within the lumen of the body for at least partially moving the sealing member into the reduced cross-sectional region of the lumen in the body, thereby deflecting the shoulders towards one another or otherwise compressing the sealing member to at least partially seal the lumen in the body and/or the lumen in the sealing member.

Optionally, the proximal end of the body may include a proximal opening including a major axis and a minor axis, e.g., an elliptical opening, and the outer member may include opposing elements on its distal end. The opposing elements may be movable away from one another to define a major axis that substantially engages the proximal opening to secure the body to the distal end of the outer member.

To create this engagement, the inner member may include one or more flared regions on its distal end. The inner member may be movable proximally relative to the outer member such that the one or more flared regions slidably engage the opposing elements to move the opposing elements away from one another to engage the walls defining the proximal opening in the body. In addition, the inner member may be movable distally relative to the outer member for disengaging the opposing elements on the outer member from the proximal end of the body. The sealing member may be directed at least partially into the reduced cross-sectional region of the lumen in the body as the inner member is moved distally, thereby deflecting the shoulders on the sealing member towards one another or otherwise compressing the sealing member to at least partially seal the lumen in the body and/or the lumen in the sealing member.

In accordance with still another aspect of the present invention, a method is provided for sealing a passage through tissue from a patient's skin to a body lumen. Initially, a guide wire element is provided that extends from the patient's skin through the passage and into the body lumen.

A plug member, e.g., a generally annular body, may be advanced into the passage over the guide wire element, the body including a lumen through which the guide wire element is inserted as the body is advanced into the passage. The body may include a sealing member therein at least partially surrounding the guide wire element. The sealing member may include a lumen concentric with the lumen in the body such that the guide wire element may be inserted through both lumens.

In a preferred embodiment, the body includes an external thread pattern, and the body may be advanced into the passage by rotating the body, thereby threading the body into the passage. A handle device may be coupled to the body such that the handle device may be rotated, thereby threading the body into the passage. Once a desired location is reached, the body may be deployed from the handle device.

While or before the body is deployed, the sealing member may be directed into a reduced cross-sectional region of the lumen in the body, thereby compressing the sealing member to at least partially seal the lumen. Preferably, a plurality of shoulders on the sealing member are deflected towards one another as the sealing member is directed into the reduced cross-sectional region to at least partially seal the lumen. All or a portion of the guide wire element may be withdrawn from the passage, i.e., through the body and/or handle device, before compressing the sealing member into the reduced cross-sectional region. For example, in one method, the entire guide wire element may be withdrawn before the sealing member is compressed to seal the lumen. Alternatively, at least a portion of the guide wire element may remain within the sealing member as it compressed, as described further below.

In accordance with another aspect of the present invention, a guide wire or positioning device is provided that includes one or more wires including a proximal end and one or more lateral elements on a distal end thereof. The guide wire element may include one or more visual markers on the proximal end thereof, the markers being located a predetermined distance from the lateral elements. Preferably, the predetermined distance corresponds to a length of the delivery device and the plug member carried thereby for providing a visual indication of the relative location of the lateral elements and the distal end of the plug member when the visual marker is visible beyond the proximal end of the delivery device.

In one embodiment, the lateral elements may include one or more expandable wings, and preferably, at least two opposing wings, that may be actuable from the proximal end of the guide wire element for selectively expanding and collapsing the wings. In a preferred embodiment, the guide wire element includes an elongate outer wire including proximal and distal ends, one or more wings or expandable positioning elements adjacent the distal end, one or more wings or expandable actuator elements adjacent the proximal end, and an intermediate region extending between the positioning and actuator elements.

The guide wire element also includes an elongate inner wire including proximal and distal ends that are fixed relative to the proximal and distal ends of the outer wire. The intermediate region of the outer wire may be movable axially relative to the inner wire for expanding and collapsing the positioning and actuator elements. Preferably, the positioning elements are collapsed when the actuator elements are expanded. The positioning elements may be expanded by compressing the actuator elements inwardly, thereby directing the intermediate region of the outer wire towards the distal end, and causing the positioning elements to buckle or otherwise expand radially outwardly. The positioning elements may be biased to the collapsed configuration, e.g., such that when a constraining force on the actuator elements is removed, the positioning elements may automatically return towards the collapsed configuration.

Alternatively, the proximal end of the inner wire may be movable axially relative to the outer wire. For example, a handle may extend from the proximal end of the inner wire, such that the handle may be directed proximally to buckle or otherwise expand the positioning elements. In addition or alternatively, a spring element may be coupled between the inner and outer wires for biasing the positioning and actuator elements towards one of the collapsed and expanded configurations. Preferably, the spring biases the positioning elements to collapse towards the collapsed configuration when the handle is released.

In accordance with yet another aspect of the present invention, an apparatus is provided for sealing a passage through tissue in a body that includes an elongate delivery device including a lumen extending between proximal and distal ends thereof, and defining a longitudinal axis. A plug member, such as that described above, may be detachably carried by the distal end of the delivery device that includes a lumen communicating with the lumen of the delivery device.

The apparatus may also include a guide wire element including a proximal end receivable through the lumens in the plug member and the delivery device. The guide wire element may include one or more lateral elements on a distal end thereof, for example, one or more expandable wings or legs, as described above. The guide wire element may include one or more visual markers on the proximal end thereof that are located a predetermined distance from the lateral elements.

In one embodiment, the lateral elements may include one or more expandable wings, and preferably, at least two opposing wings, that may be actuable from the proximal end of the guide wire element for selectively expanding and collapsing the wings, as described above. In another embodiment, the lateral elements may include legs that are biased to extend transversely relative to a longitudinal axis of the guide wire element, but may be deflected to a collapsed configuration to facilitate advancing the guide wire element into a passage through tissue.

In accordance with still another aspect of the present invention, a method is provided for sealing a passage through tissue from a patient's skin to a body lumen. A distal end of a guide wire element may be advanced from the patient's skin through the passage and into a body lumen, e.g., through a percutaneous puncture communicating with a blood vessel. One or more lateral elements on the distal end of the guide wire element may be expanded within the body lumen, and the guide wire element may be at least partially withdrawn from the body lumen until the one or more lateral elements contact a wall of the body lumen.

A proximal end of the guide wire element may be inserted into a lumen of a plug member, and the plug member may be advanced into the passage over the guide wire element. In a preferred embodiment, the plug member may include an external thread pattern, and the plug member may be advanced by rotating the plug member, thereby threading the plug member into the passage.

The plug member may be advanced into the passage until the plug member is disposed adjacent to the one or more lateral elements. The plug member may be carried on a distal end of a delivery device, and the plug member may be released from the distal end of the delivery device after the plug member is advanced into the passage. For example, the guide wire element may include a marker on a proximal portion thereof that is located a predetermined distance from the one or more lateral elements. The plug member may be released from the delivery device when the marker appears from a proximal end of the delivery device, thereby deploying the plug member adjacent to the one or more lateral elements. Alternatively, the plug member may be released from the delivery device after the plug member contacts the one or more lateral elements.

A sealing member within the lumen in the plug member may be directed into a reduced cross-sectional region of the lumen, thereby at least partially sealing the lumen. Preferably, the sealing member is compressed before or as the plug member is deployed from the delivery device.

At least a portion of the guide wire element may be withdrawn from the passage, i.e., through the lumen of the plug member. For example, the one or more lateral elements may be collapsed, and the guide wire element may be withdrawn through the lumen of the plug member and removed entirely from the passage. Preferably, the guide wire element is withdrawn before the sealing member is compressed to seal the lumen in the plug member.

In accordance with another aspect of the present invention, a device for sealing a passage through tissue is provided that includes a plug member, such as those described above, including a lumen extending between proximal and distal ends thereof, and a guide wire element including a proximal end receivable through the lumen in the plug member. The guide wire element may include one or more lateral elements on a distal portion thereof, the one or more lateral elements being deflectable from an expanded configuration towards a collapsed configuration. Optionally, the guide wire element may be tubular including a bleed back lumen extending between the proximal and distal ends.

The distal portion of the guide wire element may be severable from a proximal portion of the guide wire element. The body and at least the distal portion of the guide wire element may be formed from biocompatible material, and preferably from bioabsorbable material, such that the body and the distal portion of the guide wire element may be released within a passage through tissue.

In a preferred embodiment, the lateral elements include a pair of opposing legs extending away from one another in the expanded configuration. More preferably, the opposing legs define a cross-section that is larger than the lumen in the plug member in the expanded configuration.

In accordance with yet another aspect of the present invention, an apparatus is provided for sealing a passage through tissue in a body that includes an elongate delivery device including a lumen extending between proximal and distal ends thereof, and defining a longitudinal axis. A plug member is detachably carried by the distal end of the delivery device that includes a lumen communicating with the lumen of the delivery device.

A guide wire element is also provided that includes a proximal end receivable through the lumens in the plug member and the delivery device. The guide wire element includes one or more lateral elements on a distal portion thereof, the one or more lateral elements being deflectable from an expanded configuration towards a collapsed configuration, the distal portion being severable from a proximal portion of the guide wire element. Preferably, the plug member and the distal portion of the guide wire element are formed from at least partially from bioabsorbable material.

The guide wire element may include a visual marker on the proximal end thereof, the marker being located a predetermined distance from the one or more lateral elements. The predetermined distance may correspond to a length of the delivery device and the plug member carried thereby for providing a visual indication of the relative location of the one or more lateral elements and the distal end of the plug member when the visual marker is visible beyond the proximal end of the delivery device. In addition or alternatively, the guide wire element may include a bleed back lumen extending between its proximal and distal ends.

In addition, the plug member may include a sealing member slidably disposed within the lumen of the plug member. In one embodiment, the sealing member may include a plurality of shoulders disposed about a lumen of the sealing member, the shoulders being deflectable towards one another for at least partially sealing the lumen of the sealing member.

The sealing member may be movable into a reduced cross-sectional region of the lumen in the plug member for at least partially sealing the lumen in the plug member. The sealing member may also engage a portion of the distal portion of the guide wire element when the sealing member is moved into the reduced cross-sectional region of the lumen in the plug member, thereby substantially securing the distal portion of the guide wire element to the plug member. If the guide wire element includes a bleed back lumen, the sealing member may compress the guide wire element to seal the bleed back lumen when the sealing member is compressed in the reduced cross-sectional region.

In addition, the apparatus may include a cutting element for severing the distal portion of the guide wire element from a proximal portion thereof.

In accordance with still another aspect of the present invention, a method is provided for sealing a passage through tissue from a patient's skin to a body lumen. A distal end of a guide wire element may be advanced from the patient's skin through the passage and into the body lumen, e.g., through a percutaneous puncture into a blood vessel. The guide wire element may include one or more lateral elements on the distal end of the guide wire element, which may be collapsed inwardly as the guide wire element is advanced through tissue, e.g., to reduce the guide wire element's profile and facilitate advancement through the passage. Optionally, the guide wire element may include a bleed back lumen that extends between its proximal and distal ends, providing a visual indicator when the distal end has entered the body lumen.

Once the distal end enters the body lumen, the lateral elements may automatically return to a transverse, expanded configuration. The guide wire element may be partially withdrawn from the body lumen until the one or more lateral elements contact a wall of the body lumen, thereby providing a tactile indication that the distal end of the guide wire element is disposed adjacent the wall of the body lumen.

A proximal end of the guide wire element may be inserted into a lumen of a plug member, and the plug member may be advanced into the passage over the guide wire element. In one embodiment, the plug member may include an external thread pattern, and may be advanced by rotating the plug member, thereby threading the plug member through the passage. The plug member may be advanced into the passage until the plug member is disposed adjacent to the one or more lateral elements.

A distal portion of the guide wire element may be secured relative to the plug member with the one or more lateral elements disposed substantially against the wall of the body lumen. For example, the plug member may include a sealing member therein at least partially surrounding the guide wire element. The sealing member may be directed into a reduced cross-sectional region of the lumen, thereby securing the distal portion of the guide wire element to the plug member. If the guide wire element includes a bleed back lumen, the sealing member may also compress the guide wire element to substantially seal the bleed back lumen. In addition, the sealing member may at least partially seal the lumen in the plug member as the sealing member is directed into the reduced cross-sectional region of the lumen.

A proximal portion of the guide wire element may be removed from the passage, leaving the plug member to substantially seal and/or close the passage, with the distal portion of the guide wire element secured to the plug member. For example, a cutting element may be introduced into the passage to cut or otherwise sever the guide wire element at a location proximal to the plug member, whereupon the proximal portion may be withdrawn from the passage.

Other objects and features of the present invention will become apparent from consideration of the following description taken in conjunction with the accompanying drawings.

DETAILED DESCRIPTION OF THE PREFERRED EMBODIMENTS

Figure 1A:
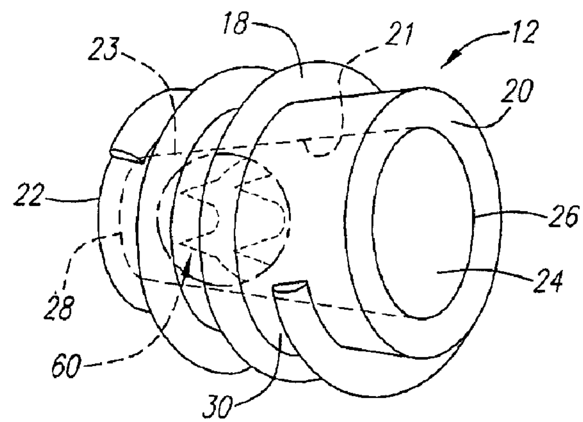
FIG. 1A is a perspective view of a plug-member, in accordance with the present invention.
Figure 1B:
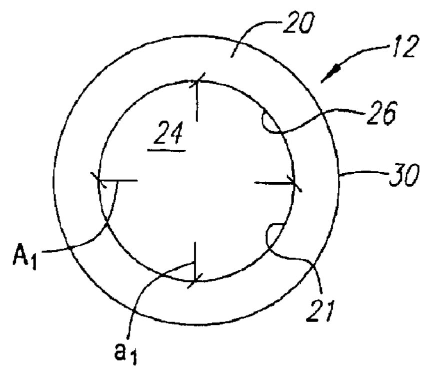
FIG. 1B is an end view of the proximal end of the plug member of FIG. 1A.
Figure 1C:
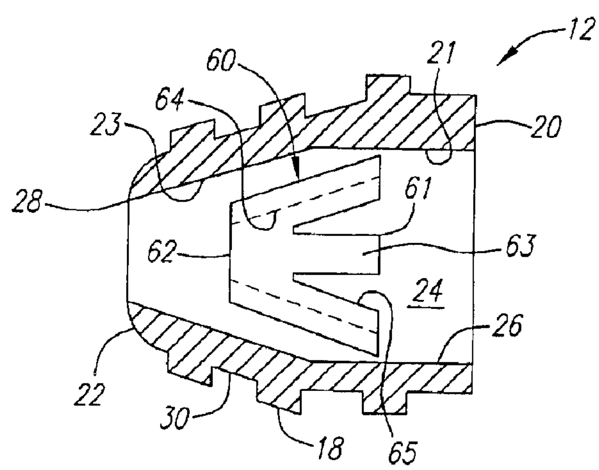
FIG. 1C is a cross-sectional side view of the plug member of FIG. 1A, including a collet disposed therein, in accordance with the present invention.

Turning now to the drawings, FIGS. 1A, 1B, and 1C show a first preferred embodiment of a plug member 12 for sealing a passage through tissue (not shown), in accordance with the present invention. The plug member 12 is a substantially rigid body, preferably having a generally cylindrical shape, including a proximal end 20, a distal end 22, and an outer surface 30. The plug member 12 includes a lumen 24 that extends between a proximal opening 26 and a distal opening or port 28.

The plug member 12 may be formed from a biocompatible material, e.g., a plastic, such as polyethylene or polyester. Preferably, the plug member 12 is formed at least partially (and more preferably entirely) from bioabsorbable material, such as collagen, polyglycolic acids (PGA's), polyactides (PLA's), and the like, which may be at least partially absorbed by the patient's body over time. Alternatively, the plug member 12 may be a semi-rigid or flexible body or may have a substantially flexible distal tip (not shown), e.g., to facilitate substantially atraumatically inserting the plug member 12 into a passage.

The plug member 12 may have a substantially uniform outer cross-section defined by outer surface 30 or may be tapered along its length. In addition, the distal end 22 may be rounded to facilitate advancing the plug member 12 into a passage through tissue. In a preferred embodiment, the plug member 12 has a length of not more than about ten millimeters (10 mm), and more preferably between about one and ten millimeters (1–10 mm). The plug member 12 also preferably has a diameter of between about one and twenty millimeters (1–20 mm). Preferably, the length and diameter have a ratio that is not more than about two-to-one.

The plug member 12 generally includes a helical thread pattern 18, including one or more helical threads, that extends at least partially between its proximal and distal ends 20, 22. Preferably, the thread pattern 18 extends completely to the distal end 22 of the plug member 12, and may be tapered at the distal end 22 to facilitate introduction into a passage through tissue (not shown). The helical thread 18 is preferably substantially rigid and may have a substantially square cross-section to facilitate sealing of a passage into which the plug member 12 is threaded. The helical thread 18 may be substantially continuous, i.e., extending helically around the outer surface 30 or, alternatively, may be intermittent (not shown). Alternatively, other features may be provided on the outer surface 30 instead of or in addition to the helical thread 30, e.g., flutes, ribs, ridges, and the like (not shown).

In a preferred embodiment, the helical thread 18 is integrally formed on the outer surface 30 of the plug member 12. For example, the plug member 12 and thread 18 may both be formed as a unitary structure, e.g., by injection molding. Alternatively, the threads may be cut or otherwise formed in the outer surface 30 of the plug member 12 after the plug member 12 is formed. In a further alternative, the thread pattern may be eliminated, thereby providing a substantially smooth outer surface (not shown).

The lumen 24 extending through the plug member 12 may include a proximal region 21 and a tapered distal region 23, the distal region 23 tapering inwardly away from the proximal region 21 towards the distal opening 28. Thus, the distal region 23 near the proximal region 21 may define a larger cross-section lumen 24 than the distal region 23 near the distal opening 28.

The proximal region 21 of the lumen 24 may be elliptical in cross-section, while the outer surface 30 of the plug member 12 may be substantially round. Thus, the proximal region 21 of the lumen 24 may include a major axis $A_1$ and a minor axis $a_1$ (best seen in FIG. 1B). The major and minor axes $A_1$, $a_1$ of the proximal region 21 of the lumen 24, together with corresponding axes on a handle device 14 (not shown, see, e.g., FIGS. 3–4B), may provide a locking mechanism between the plug member 12 and the handle device 14, as described further below.

A collet or sealing member 60 may be disposed within the lumen 24 of the plug member 12 that may be movable axially therein, e.g., from within the proximal region 21 towards the distal end 22 of the plug member 12. The collet 60 may be a generally annular body including a proximal end 61, a distal end 62, and a lumen 64 (best seen in FIGS. 2A–2D) extending between the proximal and distal ends 60, 62. When the collet 60 is disposed within the plug member 12, the lumen 64 of the collet 60 may be in fluid communication with the lumen 24 of the plug member 12. Also, when placed within the lumen 24 of the plug member 12, the collet 60 may be sufficiently flexible to generally conform to the shape of the lumen 24. For example, if the lumen 24 of the plug member 12 is tapered along its length and/or has an elliptical cross-section, as shown in FIGS. 1A–1C, the collet 60, when placed within lumen 24, may also become tapered along its length and/or assume an elliptical cross-section.

Alternatively, other sealing members may be provided instead of the collet 60. For example, an annular member, e.g., a helically wound sheet of material or a solid annular body, may be provided that is compressible (not shown). Exemplary embodiments of a sealing member that may be incorporated into the plug member 12 are disclosed in application Ser. No. 09/866,548, filed May 25, 2001, incorporated by reference herein.

Turning to FIGS. 2A–2D, a preferred embodiment of the collet 60 is shown that includes a proximal end 61 and a distal end 62 defining a lumen 64 therebetween. The collet 60 also has a proximal opening 66 and a distal opening 68 that are located at the proximal and distal ends 61, 62, respectively, and communicating with the lumen 64, respectively. A plurality of radial slots 65 may be formed in the proximal end 61 that are oriented inwardly towards the lumen 64, thereby defining a plurality of flexible or semi-rigid shoulders 63 disposed circumferentially about the lumen 64.

The collet 60 may be formed from a biocompatible material, e.g., a plastic, such as polyethylene or polyester. Preferably, the collet 60 is formed at least partially (and more preferably entirely) from bioabsorbable material, such as collagen, polyglycolic acids (PGA's), polyactides (PLA's), and the like, similar to the plug member 12. In addition or alternatively, the collet 60 may be formed from a material that expands when exposed to fluids, e.g., collagen and/or an expandable foam. Exemplary materials that may be appropriate for use in the collet 60 and/or the plug member 12 are disclosed in U.S. Pat. No. 6,224,630, the disclosure of which is expressly incorporated herein by reference. In addition, all or a portion of the collet 60 may be coated with a therapeutic substance, such as a thrombogenic material, e.g., along the lumen 64.

Figure 2A:
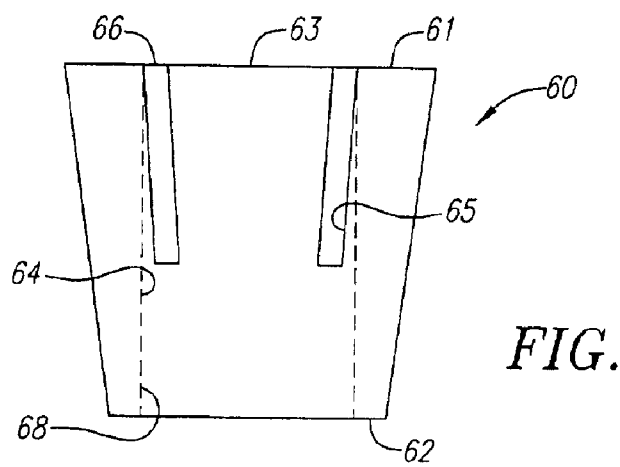
FIG. 2A is a side view of a first embodiment of the collet shown in FIG. 1C.
Figure 2B:
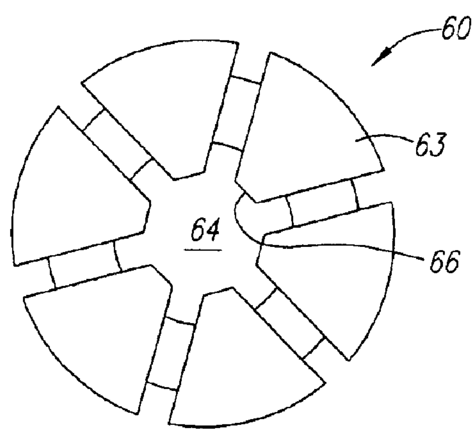
FIGS. 2B and 2C are end views of a proximal end of the collet of FIG. 2A in open and closed positions, respectively.

Preferably, the collet 60 is more flexible than the plug member 12, thereby enabling the collet 60 to conform substantially to the contours of the lumen 24 of the plug member 12. The collet 60 may adopt a circular cross-section when in a relaxed state (free from external constraints or forces), as best seen in FIG. 2B. Once placed within the lumen 24 of the plug member 12, however, the collet 60 may conform substantially to the contours of the lumen 24. For example, when placed within a lumen 24 that is elliptical in cross-section, as shown in FIG. 1B, the collet 60 may also become substantially elliptical in cross-section.

As best seen in FIG. 2B, the shoulders 63 are arranged around the lumen 64 and initially define an expanded or open position. In the open position, the slots 65 space apart adjacent shoulders 63 and the inner edges 67 of the shoulders 63 define a relatively open proximal opening 66. Therefore, in the open position, fluid is able to flow relatively freely through the proximal opening 66 and the lumen 64.

Figure 2C:
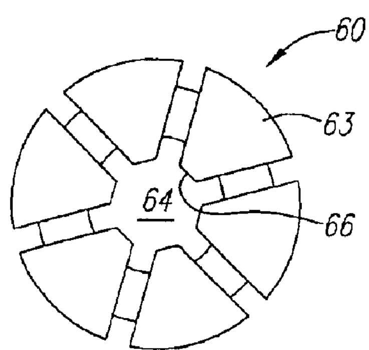
Figure 2D:
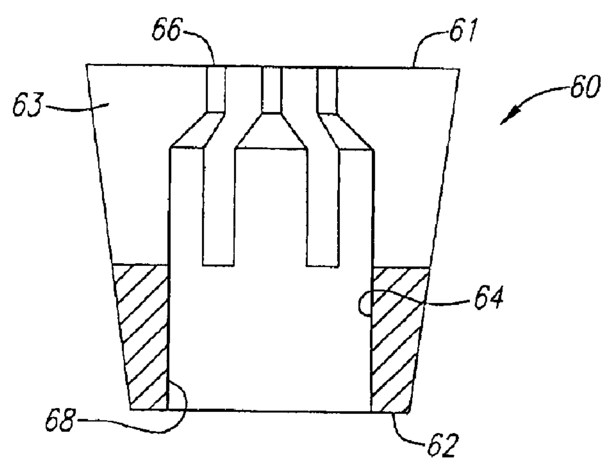
FIG. 2D is a cross-sectional side view of the collet of FIG. 2A.

Turning to FIG. 2C, the shoulders 63 are sufficiently flexible that they may be deflected inwardly towards one another, thereby defining a closed position. In the closed position, the inner edges 67 move towards one another such that the proximal opening 66 is substantially smaller, and may be entirely closed. In the closed position, fluid flow through the proximal opening 66 is restricted, and may be substantially completely obstructed, compared to the open position. Thus, the collet 60 may be compressed to substantially seal the lumen 24 from fluid flow therethrough when the collet 60 is in the closed position.

The shoulders 63 of the collet 60 may be deflected from the open position towards the closed position by exerting an inward force on the shoulders 63. For example, with the collet 63 disposed within the plug member 12, as shown in FIG. 1C, a distal force "F" may be applied to the proximal end 61 of the collet 60. This may cause the collet 60 to enter and move distally into the tapered region 23 of the lumen 24, thereby subjecting the shoulders 63 to an inward force that causes the shoulders 63 to deflect inwardly towards the closed position (not shown in FIG. 1C, see, e.g., FIG. 2C).

Turning to FIGS. 3 and 4A–4E, the plug member 12 may be incorporated into an apparatus 10 for sealing a passage through tissue. Generally, the apparatus 10 includes a handle or delivery device 14 for carrying the plug member 12 and/or a guide wire element 16 for positioning the plug member 12 during delivery. The handle device 14 generally includes an tubular outer member 80 and an elongate inner member 70 slidably received in the outer member 80. The components of the handle device 14 may be formed from conventional biocompatible materials, e.g., plastic, such as polyethylene or polyester, and/or metal, such as stainless steel. The handle device 14 preferably has a cross-section that is generally smaller than a cross-section of the plug member 12, e.g., to minimize dilation of a passage into which the apparatus 10 is inserted.

Figure 4A:
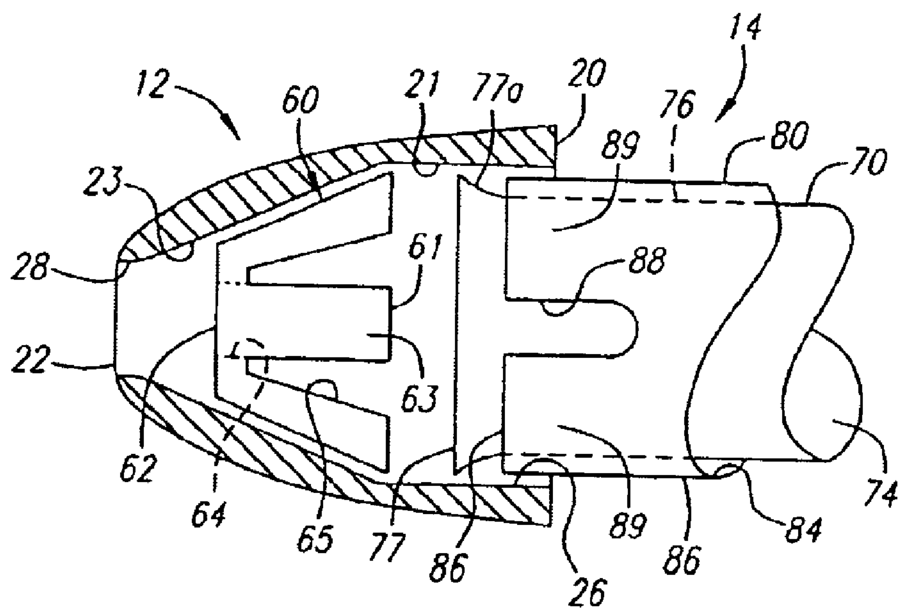
FIGS. 4A–4D are cross-sectional views of the distal end of the apparatus of FIG. 3, during various stages of deploying the plug member.
Figure 4B:
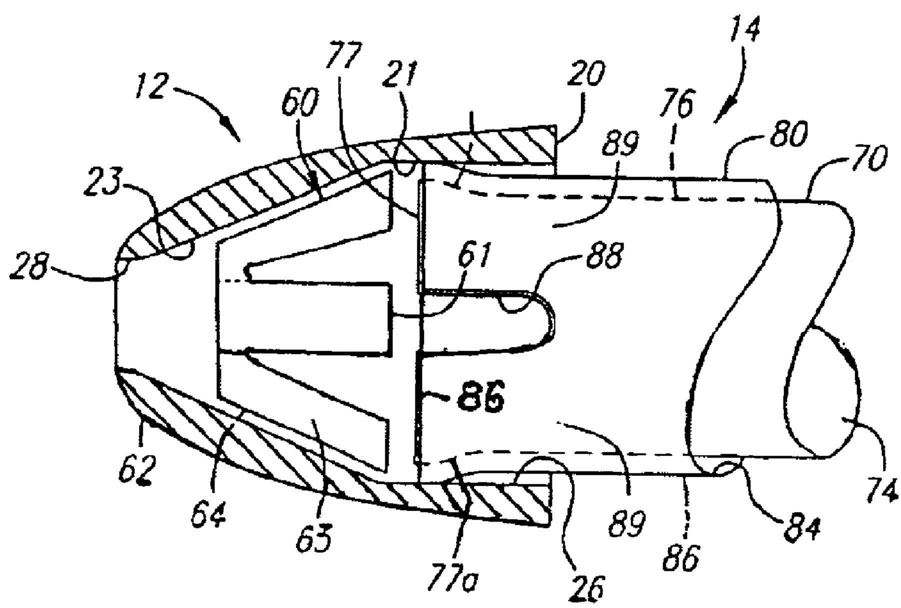
Figure 4C:
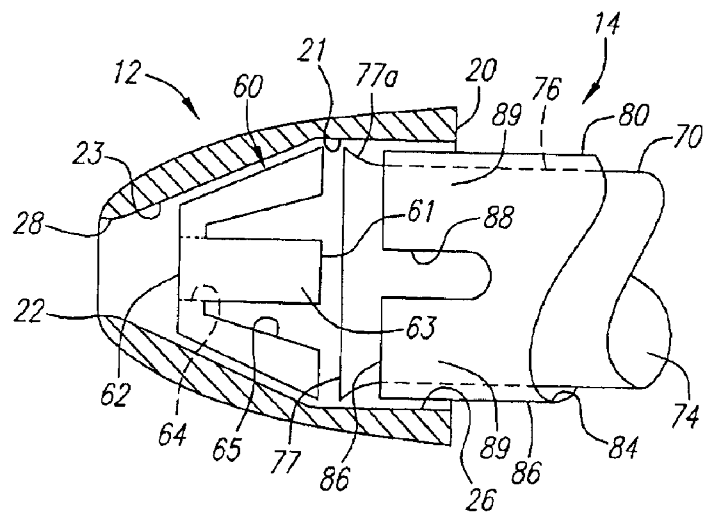
Figure 4D:
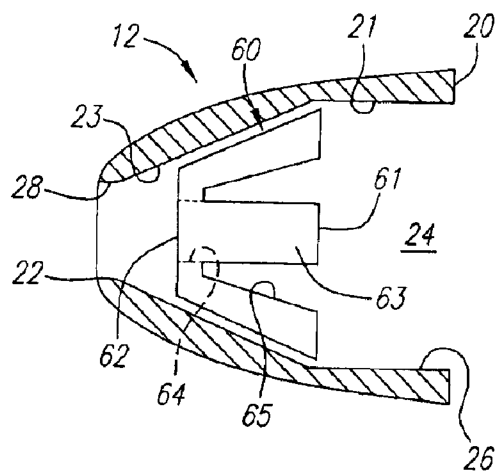
Figure 4E:
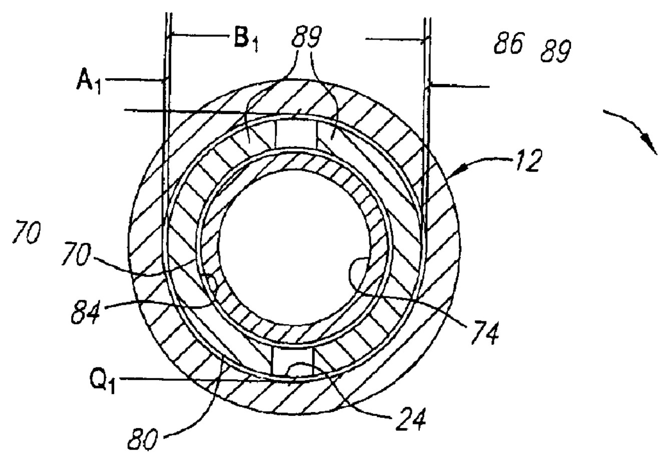
FIG. 4E is a cross-sectional view of the distal end of the apparatus of FIGS. 3 and 4B, taken along line 4E—4E.

With particular reference to FIGS. 4A–4E, the inner member 70 may be substantially rigid, and preferably is a tubular body including a lumen 74 (best seen in FIG. 4E) extending between a proximal end (not shown) and a distal end 76 of the inner member 70. As best seen in FIGS. 4A–4C, the distal end 76 of the inner member 70 preferably includes one or more flared regions that extend radially outwardly. The flared region may be a substantially continuous flared ridge 77 including a ramped surface 77*a* extending around a circumference of the distal end 76 and having a cross-section that is larger than the balance of the inner member 70. The flared ridge 77 may have an elliptical shape, as shown in FIG. 4E, although alternatively, the flared ridge may have a substantially circular shape (not shown). In a further alternative, the distal end 76 of the inner member 70 may include a plurality of ramps (not shown) extending from an outer surface of the inner member 70, e.g., in pairs opposite one another about the circumference of the inner member 70.

Returning to FIGS. 3 and 4A–4E, the outer member 80 may be a semi-rigid or flexible tubular body including a proximal end 81 (best seen in FIG. 3), a distal end 86, and a lumen 84 extending between the proximal and distal ends 80, 86. As shown in FIGS. 4A–4C, the outer member 80 may also include a plurality of slots 88 that extend proximally from the distal end 86 a relatively short distance (compared to a length of the outer member 80). Preferably, as best seen in FIG. 4E, a pair of opposing slots 88 are provided that divide the distal end 86 into opposing halves 89. The slots 88 enable the opposing halves 89 to expand or otherwise move away from one another to increase the cross-section of the distal end 86, as explained further below.

Figure 3:
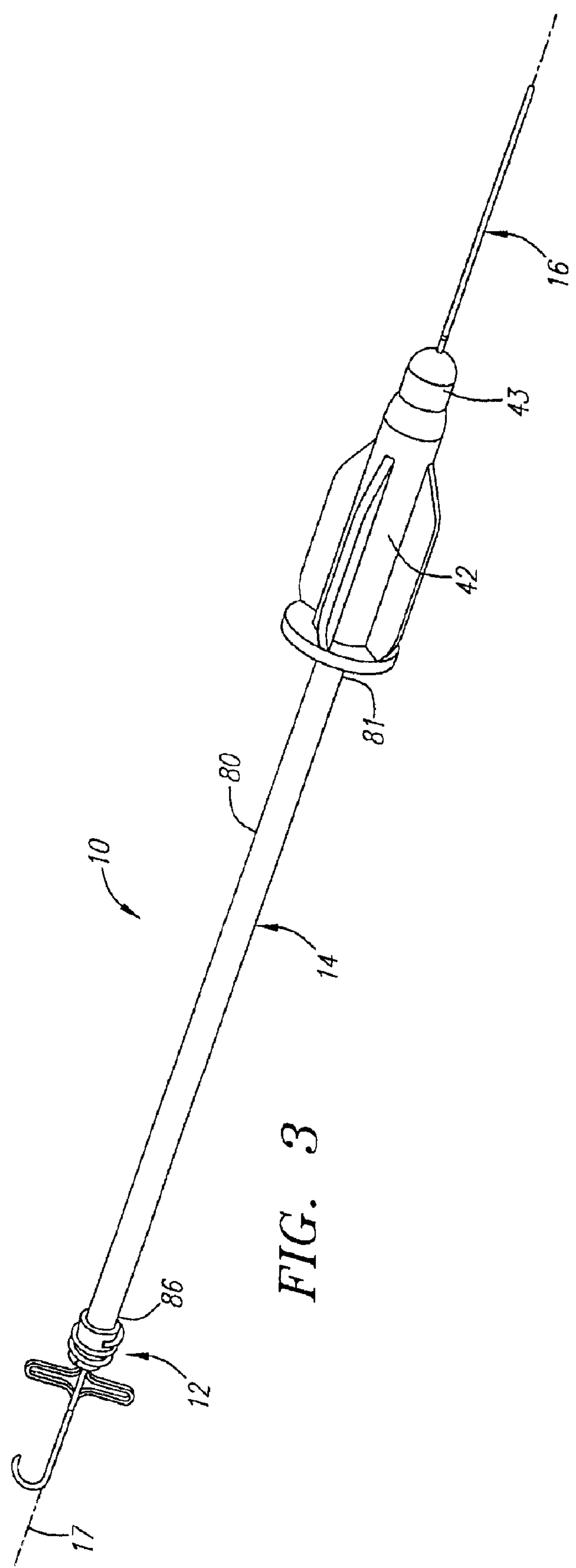
FIG. 3 is a perspective view of an apparatus for delivering a plug member, in accordance with the present invention.

Turning to FIG. 3, a handle 42 is attached to or otherwise extends from the proximal end 81 of the outer member 80. An actuator, e.g., button 43, extends into the handle 42 that is coupled to the proximal end of the inner member 70 (not shown in FIG. 3) slidably received in the outer member 80. Axial movement of the inner member 70 relative to the outer member 80 may be limited, e.g., by the button 42 and/or the flared ridge 77.

For example, as shown in FIG. 4B, the inner member 70 may be positioned in a first or proximal position such that the flared ridge 77 is disposed at least partially within the distal end 86 of the outer member 80, causing the opposing halves 89 to be expanded outwardly away from one another, and thereby increasing a major axis dimension $B_1$ of the outer member 80 (shown in FIG. 4E). By depressing the button 43, the inner member 70 may be directed distally relative to the outer member 80, e.g., to advance the flared ridge 77 out of the distal end 86 of the outer member 80, as shown in FIG. 4C. The distal end 86 of the outer member 80 may simply be relaxed when the flared ridge 77 is removed or may be sufficiently resilient that the opposing halves 89 return at least partially towards one another.

This expansion of the distal end of the outer member 80 may be used to substantially secure the plug member 12 to the handle device 14. Turning to FIG. 4A, with the flared ridge 77 outside the distal end 86 of the outer member 80, the distal end 81 of the outer member 80 may be inserted into the proximal end 20 of the plug member 12. If the plug member 12 includes a lumen 24 with an elliptical shaped proximal region, the slots 88 on the outer member 80 are preferably aligned with the minor axis $a_1$ of the proximal region 21, as best seen in FIG. 4E. The inner member 70 may then be directed proximally such that the ramped surface 77*a* of the flared ridge 77 slidably engages and, consequently, expands the opposing halves 89 of the outer member 80 into engagement with the plug member 12. The major axis $B_1$ of the outer member 80 may increase substantially to the major axis $A_1$ of the proximal region 21 of the lumen 24, i.e., until the opposing halves 89 frictionally engage the plug member 12. Preferably, this frictional engagement is sufficiently strong that the plug member 12 is substantially fixed relative to the outer member 80. Consequently, any rotational force applied to the outer member 80, e.g., to the handle 42, may be translated to the plug member 12 without allowing the plug member 12 to slip substantially relative to the outer member 80.

During delivery of the plug member 12 to close a passage through tissue, as explained further below, the handle device 14 may be used to deploy the plug member 12 from the outer member 80 and/or to compress the collet 60 within the plug member 12 to substantially seal the lumen 24 through the plug member 12. For example, the button 43 may be depressed partially to advance the flared ridge 77 substantially out of the distal end 86 of the outer member 80 (as shown in FIG. 4A), thereby relaxing the opposing halves 89 and substantially reducing the frictional force securing the plug member 12 to the outer member 80. Depressing the button 43 may also direct the distal end 76 of the inner member 70 into contact with the proximal end 61 of the collet 60 within the lumen 24 in the plug member 12 and cause the collet 60 to move distally within the lumen 24. Preferably, this causes the collet 60 to travel distally at least partially into or along the tapered distal region 23 of the lumen 24 (as shown in FIG. 4C), thereby compressing the shoulders 63 towards one another to close the opening 66 therein, as explained above. Once the collet 60 is forced into the distal region 23 of the lumen 24, continued depression of the button 43 may cause the entire plug member 12 to be directed distally relative to the distal end 86 of the outer member 80, e.g., to deploy the plug member 12 from the handle device 14.

Figure 11A:
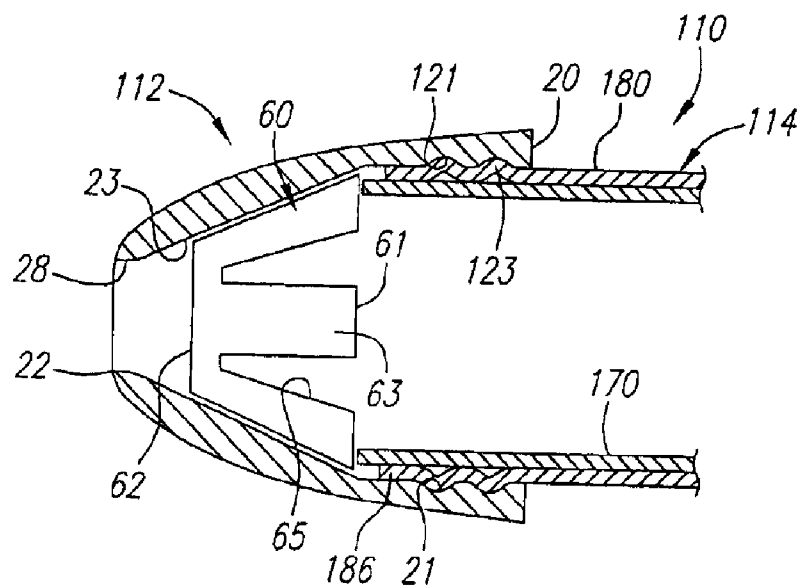
FIG. 11A is a cross-sectional view of an alternative embodiment of an apparatus for delivering a plug member, in accordance with the present invention.
Figure 11B:
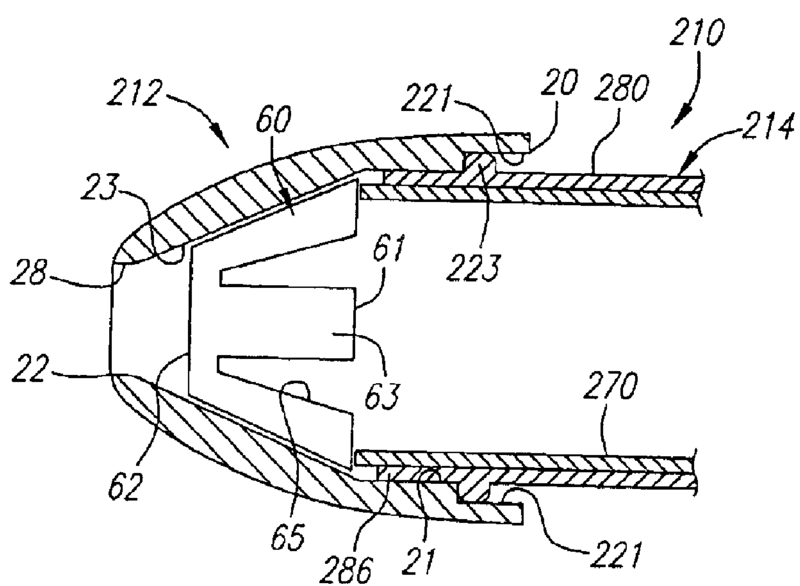
FIG. 11B is a cross-sectional view of yet another alternative embodiment of an apparatus for delivering a plug member, in accordance with the present invention.

Turning to FIGS. 11A and 11B, alternative embodiments of an apparatus 110, 210 are shown that include a handle device 114, 214 that may be used to deliver a plug member 112, 212, which are similar to the embodiment described above. Generally, as shown in FIG. 11A, the handle device 114 includes a lumen 184 that extends between its proximal end (not shown) and its distal end 186, similar to the previous embodiment. Unlike the previous embodiment, the handle device 114 and the plug member 112 include mating threads 123, 121. Preferably, the mating threads 123, 121 extend in the same direction as the thread pattern 118 on the plug member 112. Thus, the handle device 114 may be rotated in a first direction to thread the plug member 112 through tissue, and in a second direction to unthread the plug member 112 from the handle device 114.

Turning to FIG. 11B, in a further alternative, the plug member 212 and handle device 214 may include cooperating connectors for releasably coupling the plug member 212 to the distal end 286 of the handle device 214. For example, the handle device 214 may include tabs 223 that may be received in pockets 224 in the plug member 212. Thus, as the handle device 214 is directed distally, the plug member 212 may remain secured to the distal end 286. If the handle device 214 is directed proximally, the tabs 223 may be withdrawn from the pockets 224, thereby releasing the plug member 212 from the handle device 214. Other exemplary cooperating connectors that may be incorporated into the apparatus 210 are described in application Ser. No. 09/738,431, filed Dec. 14, 2000, which is expressly incorporated by reference herein.

Figure 5A:
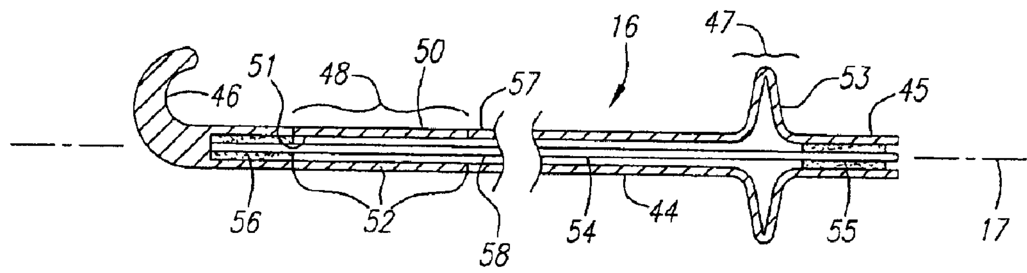
FIGS. 5A and 5B are cross-sectional views of a guide wire element of the apparatus of FIG. 3, with expandable wings thereon in collapsed and expanded configurations, respectively.
Figure 5B:
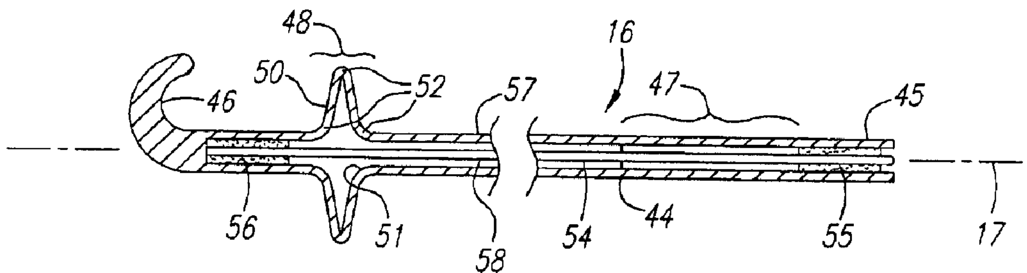

Turning to FIGS. 5A and 5B, the guide wire element 16 is generally a flexible or semi-rigid elongate member including one or more expandable elements thereon. The guide wire element 16 generally includes a tubular outer element or wire 44 and an elongate inner element or wire 54 that are at least partially slidable relative to one another. The outer wire 44 may be formed from a flexible or semi-rigid material, such as plastic, and generally includes a proximal end 45 and a distal end 46, e.g., having a "J" tip or other substantially atraumatic tip. The outer wire 44 includes a proximal actuator region 47 and a distal expandable region 48 that are coupled to one another such that as one is radially expanded, the other is radially compressed, as explained further below.

For example, as shown in FIG. 5A, in a first or collapsed configuration, the distal region 48 includes one or more wings 50 that are collapsed, e.g., extending substantially parallel to the longitudinal axis 17 of the guidewire element 16. Thus, the outer wire 44 may have a substantially uniform cross-section distal to the actuator region 47. Preferably, the outer wire 44 defines an outer diameter that is not more than about half to two millimeters (0.5–2.0 mm).

The wings 50 may be formed in the outer wire 44 by creating a plurality of longitudinal slots 51 in the wall of the outer wire 44. Living hinges or other bends 52 may be formed in the outer wire 44, e.g., by notching the wall or otherwise programming bends into the wall material, as is known in the art. Similar wings 53 may be formed in the actuator region 47 that, in the collapsed configuration, may extend radially outwardly.

Turning to FIGS. 3 and 5B, in a second or expanded configuration, the wings 50 on the distal region 48 extend radially outwardly and the wings 53 on the actuator region 47 are collapsed, e.g., extending substantially parallel to the longitudinal axis 17. In a preferred embodiment, the distal region 48 includes two opposing wings 50, as best seen in FIG. 3, although alternatively, the distal region 48 may include four or more wings (not shown). Similarly, the actuator region 47 may include any number of wings, such as the two wings 53 shown in FIG. 5A.

Referring again to FIGS. 5A and 5B, the inner wire 54 may be solid or hollow, and may be formed from conventional guide wire materials, such as stainless steel or Nitinol, such that the guide wire element 16 has sufficient column strength to resist buckling or kinking. The inner wire 54 includes a proximal portion 55 and a distal portion 56, both of which may be at least partially received within the outer wire 44. With the proximal portion 55 of the inner wire 54 disposed proximal to the actuator region 47, the proximal portion 55 may be fixed relative to the outer wire 44. For example, the proximal portion 52 of the inner wire 54 may be bonded to the inner wall of the outer wire 44, e.g., using an adhesive, sonic welding, melting, and the like. Similarly, the distal portion 56 of the inner wire 54 may be disposed distal to the distal region 48 of the outer wire 44 and fixed, e.g., to the inner wall of the outer wire 44.

Thus, an intermediate region 57 of the outer wire 44 may be freely slidable relative to an intermediate region 58 of the inner wire 54, while the respective proximal and distal ends remain fixed. This relative fixation may facilitate directing the outer wire 44 between the collapsed and expanded configurations. For example, as shown in FIG. 5A, the wings 53 on the actuator region 47 are expanded, while the wings 50 on the distal region 48 are collapsed. By compressing the wings 53 on the actuator region 47 inwardly, the intermediate region 57 of the outer wire 44 may be directed distally relative to the intermediate region 58 of the inner wire 54. This causes the wings 53 on the distal region 48 to buckle and expand until, when the wings 50 are collapsed, the wings 53 are expanded, as shown in FIG. 5B.

In one embodiment, the outer wire 44 may be biased towards the collapsed configuration. Thus, when an inwardly compressive force is removed from the wings 53 on the actuator region 47, the wings 53 may automatically expand, thereby causing the wings 53 on the distal region 48 to collapse. Alternatively, the intermediate region 57 of the outer wire 44 may be manually directed proximally, thereby collapsing the wings 50 and expanding the wings 53.

Figure 6A:
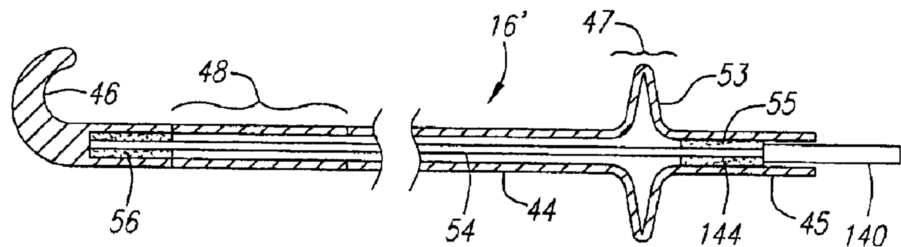
FIGS. 6A and 6B are side views of an alternative embodiment of a guide wire element having a spring element, in accordance with the present invention.
Figure 6B:
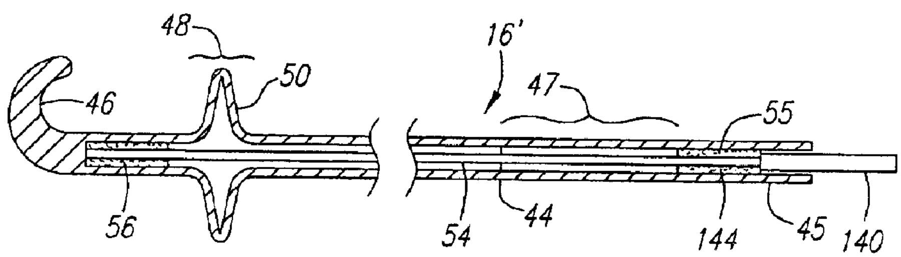

In a further alternative, shown in FIGS. 6A and 6B, guide wire element 16' may include a spring element 144 for biasing the guide wire element 16' towards one of the collapsed and expanded configurations. The guide wire element 16' shares common elements with guide wire element 16, and therefore, for simplicity, the same reference numbers have been used to identify common elements. For example, similar to the previous embodiment, the guide wire element 16' includes outer and inner wires 44, 54, the outer wire 44 including proximal and distal regions 47, 48 with wings 53, 50. Unlike the previous embodiment, the proximal portion 55 of the inner wire 54 is not fixed relative to the proximal end 45 of the outer wire 44, but is movable axially, preferably within a predetermined range.

The spring element 144 is coupled between the proximal portion 55 of the inner wire 54 and the proximal end 45 of the outer wire 44, e.g., to bias the outer wire 44 towards the collapsed configuration. Preferably, the spring element is an extension spring that is disposed concentrically around the inner wire 54, thereby minimizing a profile of the guide wire element 16'. A handle 140 may be coupled to the proximal portion 55 of the inner wire 54 that extends proximally from the proximal end 45 of the outer wire 44. Thus, the handle 140 may be pulled proximally against the bias of the spring element 144, thereby directing the inner wire 54 proximally relative to the outer wire 44 and causing the wings 50 on the distal region 48 to expand towards the expanded configuration shown in FIG. 6B. When the handle 140 is released, the spring element 144 may retract the inner wire 54 distally, thereby collapsing the wings 50.

Optionally, cooperating elements or detents may be provided on the handle 140 and/or inner wire 54, and on the outer wire 44 for limiting movement of the inner wire 54. For example, once the handle 140 has been pulled to expand the wings 50 on the distal region 48 of the outer wire 44, the handle 140 may be rotated about the longitudinal axis 17 to engage detents (not shown) on the handle 140 and the outer wire 44 to lock the guide wire element 16' in the expanded configuration. The guide wire element 16' may then be manipulated, for example, to position a plug member (not shown) within a passage through tissue (also not shown), as explained below. When it is desired to collapse the wings 50, the handle 140 may be pulled proximally and/or rotated back to disengage the detents, and then released, whereupon the spring element 144 may automatically cause the wings 50 to collapse to the collapsed configuration.

In still a further alternative, an actuator housing (not shown) may be disposed around or otherwise coupled to the guide wire element 16 for manipulating the wings 50 on the outer wire 44 between the collapsed and expanded configurations. For example, the actuator may include elements (not shown) that engage the proximal end 45 and intermediate portion 57 of the outer wire 44. The elements may direct the intermediate portion 57 axially, i.e., distally and/or proximally, relative to the proximal end 45 for expanding and/or collapsing the wings 50. In yet another alternative, a tubular sleeve (not shown) may be slidable over the guide wire element 16 to secure the wings 53 on the actuator region 47 when the outer wire 44 is in the expanded configuration.

Figure 7A:
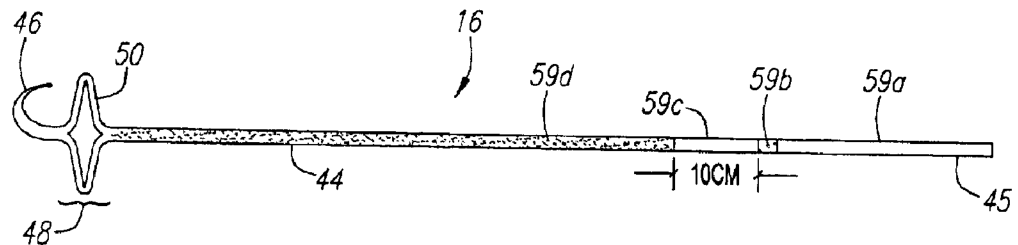
FIGS. 7A–7D are side views of a plug member and handle device being advanced over a guide wire element, and showing positioning markers on the guide wire element.

Turning to FIGS. 7A–7D, the guide wire element 16 of FIGS. 5A and 5B (or alternatively, the guide wire element 16' of FIGS. 6A and 6B) may include one or more visual indicators that facilitate positioning a handle device 14 and plug member 12 along the guide wire element 16 during delivery. For example, the outer wire 44 may include one or more contrasting color areas located at predetermined distances from the distal region 48. As best seen in FIG. 7A, the outer wire 44 may include a proximal color area 59*a*, a narrow color band 59*b*, an intermediate color area 59*c*, and a distal color area 59*d*.

The color areas 59*a*–59*d* may include any color that is suitable for casual observation by a user, with adjacent areas being different colors. For example, in one embodiment, the proximal color area 59*a* and the intermediate color area 59*c* may be white, while the narrow color band 59*b* and the distal color area 59*d* may be blue.

In addition or alternatively, the guide wire element 16 may include a bleed back lumen (not shown). For example, a lumen may be provided within the inner wire 54 that extends between its proximal and distal ends. In a further alternative, a bleed back lumen (not shown) may be provided that extends through the plug member and/or handle device.

Figure 7B:
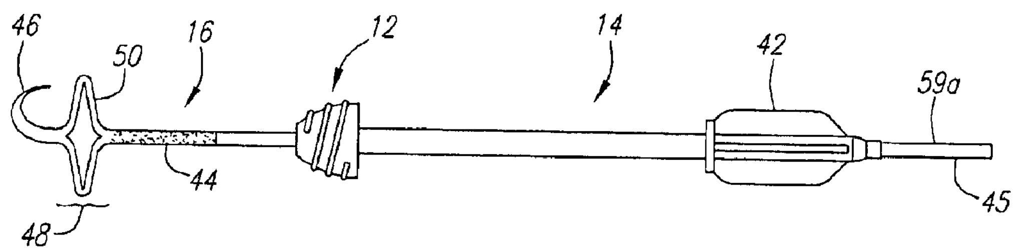
Figure 7C:
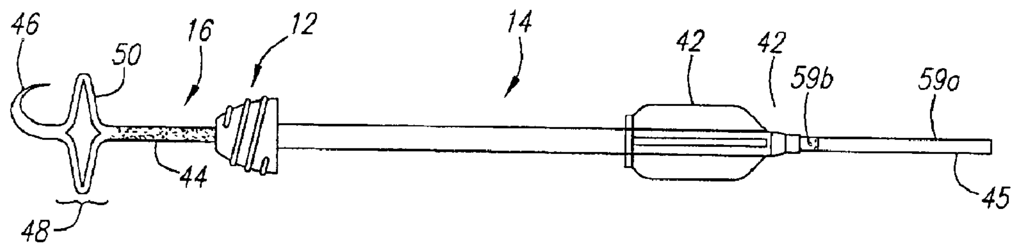
Figure 7D:
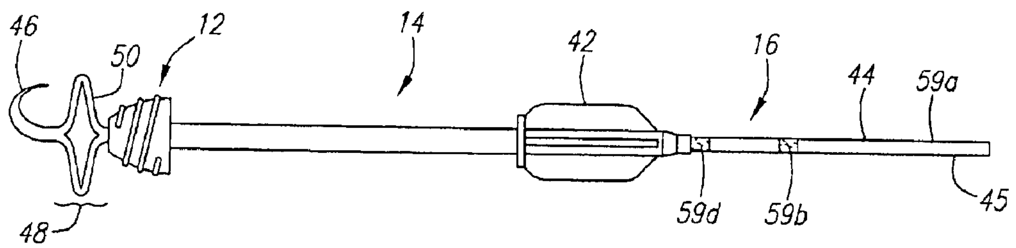

Turning to FIGS. 7B–7D, the handle device 14 with the plug member 12 carried thereby may be advanced over the guide wire element 16, e.g., during delivery of the plug member 12. For example, the handle device 14 may be advanced after the wings 50 have been expanded to the expanded configuration. As the handle device 14 is initially advanced over the guide wire element 16, the proximal color area 59*a* becomes visible beyond the handle 42 of the handle device 14, as shown in FIG. 7B.

As the handle device 14 is advanced further, the narrow color band 59*b* may becomes visible, thereby providing a warning that the plug member 12 is approaching the wings 50 on the distal region 48 of the outer wire 44, as shown in FIG. 7C. The narrow color band 59*b* may be only a few millimeters long, and the intermediate color band 59*c* may have a predetermined length, e.g., ten millimeters (10 mm). Finally, as shown in FIG. 7D, as the handle device 14 is advanced still further, the distal color area 59*d* may appear. The intermediate color area 59*c* may be located a predetermined distance from the wings 50 on the outer wire 44. Preferably, the predetermined distance corresponds to a length of the handle device 14 and plug member 12 such that when the distal color area 59*a* begins to appear, it indicates that the distal end 22 of the plug member 12 is in close proximity to the wings 50.

Turning to FIGS. 8A–8E, an apparatus 10 in accordance with the present invention may be used to close and/or seal a passage through tissue, for example, a puncture 92 extending from a patient's skin 94 through intervening tissue 96 to a blood vessel 90. Preferably, the apparatus 10 is used to deliver a plug member 12 through the passage 92 to a location in or adjacent to a wall 98 of the vessel 90 or other body lumen. The passage 92 may be a conventional percutaneous puncture created to access a peripheral vessel, for example, a femoral, carotid, or radial artery.

An introducer (not shown) may be positioned through the passage 92 into the vessel 90 in order to permit one or more instruments, e.g., guide wires, catheters, and the like (also not shown), to be advanced into the vessel 90 in order to perform a diagnostic and/or therapeutic procedure at a location within the patient's body accessible from the vessel 90. Upon completing the procedure, any instruments may be removed from the introducer, and the introducer itself may be removed from the passage 90.

Figure 8A:
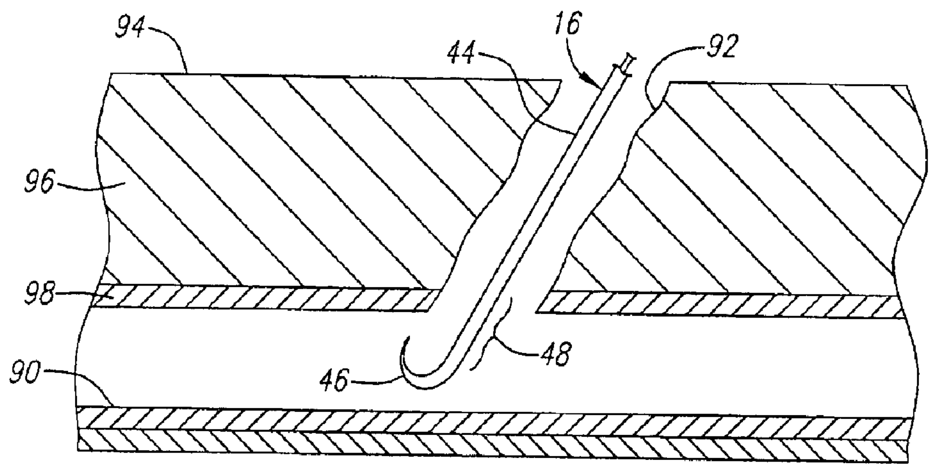
FIGS. 8A–8E are cross-sectional side views of a passage communicating with a blood vessel, showing a method for delivering a plug member to seal the passage.

Turning to FIG. 8A, with the outer wire 44 in the collapsed configuration, the guide wire element 16 may be introduced through the passage 92 until the distal region 48 is located within the vessel 90, e.g., after the introducer (not shown) has been removed from the passage 92. Alternatively, the introducer may remain in the passage 92, and the guide wire element 16 may be advanced through the introducer into the vessel 90, whereupon the introducer may be removed. If the guide wire element 16 includes a bleed back lumen (not shown), as the distal region 48 enters the vessel 90, blood may flow through the bleed back lumen and out the proximal end of the guide wire element 16 (not shown), thereby providing a visual indication that the vessel 90 has been reached.

Figure 8B:
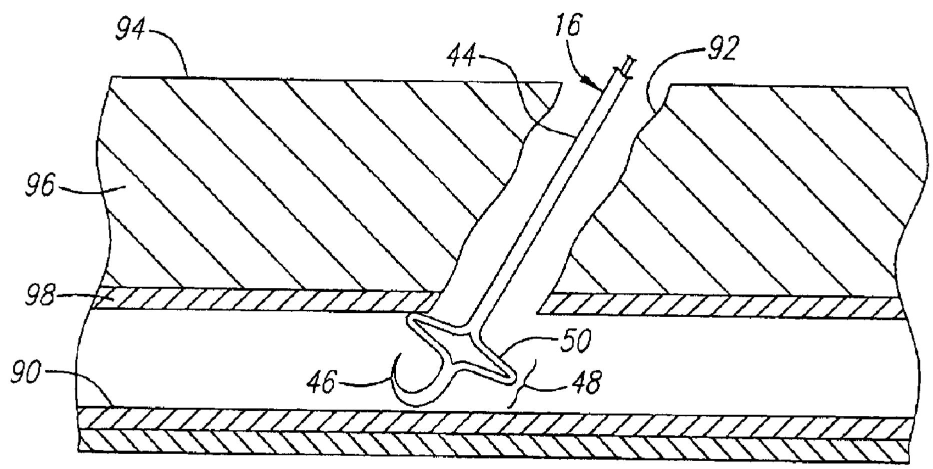
Figure 8C:
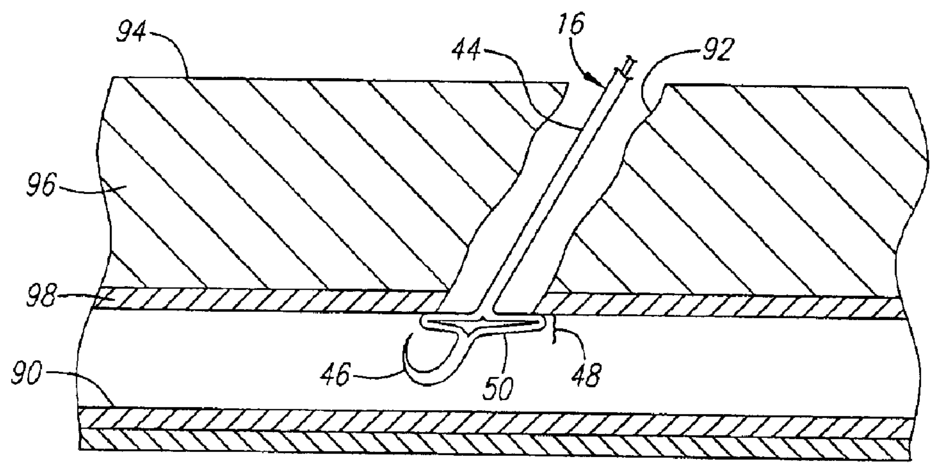

Turning to FIG. 8B, once the distal region 48 of the guide wire element 16 is positioned within the vessel 90, the wings 50 may be expanded to the expanded configuration. For example, as explained above, the wings 53 on the actuator region 47 of the guide wire element 16 may be compressed inwardly, thereby expanding the wings 50 on the distal region 48. Alternatively, a handle (not shown) on the guide wire element 16 may be pulled to expand the wings 50, also as explained above. The guide wire element 16 may then be manipulated, e.g., pulled proximally, until the wings 50 on the distal region 48 contact the wall 98 of the vessel 90, as shown in FIG. 8C, thereby providing a tactile indication of the location of the vessel 90.

The handle device 14 with the plug member 12 carried thereby may then be advanced over the guide wire element 16 and into the passage 92. If the plug member 12 includes an external thread pattern 18, the handle device 14 may be rotated to thread the plug member 12 through the passage 92 towards the vessel 90. Alternatively, if the plug member 12 includes a substantially smooth outer surface, it may be advanced axially through the passage 92 without requiring rotation of the handle member 14. With additional reference to FIG. 4B, it will be appreciated that, as the handle device 14 is advanced over the guide wire element 16, the guide wire element 16 may pass through the lumen 24 of the plug member 12, and consequently, through the lumen 64 of the collet 61 located within the plug member 12.

As explained above with reference to FIGS. 7A–7D, the guide wire element 16 may include one or more visual indicators (not shown) located a predetermined distance from the wings 50. When the visual indicators appear from the handle device 14, they indicate that the plug member 12 is located at a predetermined location relative to the wall 98 of the vessel 90. Preferably, when the visual indicators appear, the plug member 12 is located within or adjacent the wall 98 of the vessel 90, as shown in FIG. 8C.

Thus, the guide wire element 16 and the visual indicators thereon may identify the location of the vessel 90 relative to the patient's skin 94, and thereby indicate the depth to which the plug member 12 should be advanced before being deployed from the handle device 14. Alternatively, if no visual indicators are provided, the wings 50 on the guide wire element 16 may provide a tactile indication when the plug member 12 has reached a delivery location, e.g., when the distal end 22 of the plug member 12 contacts the wings 50 on the guide wire element 16. In a further alternative, the plug member 12 and/or handle device 14 may include one or more bleed back lumens for indicating when the plug member 12 has entered the vessel 90, in addition to or instead of the wings 50. Additional information on methods for delivering a plug member 12 using bleed back indicators may be found in application Ser. No. 09/866,548, filed May 25, 2001, incorporated by reference herein.

Figure 8D:
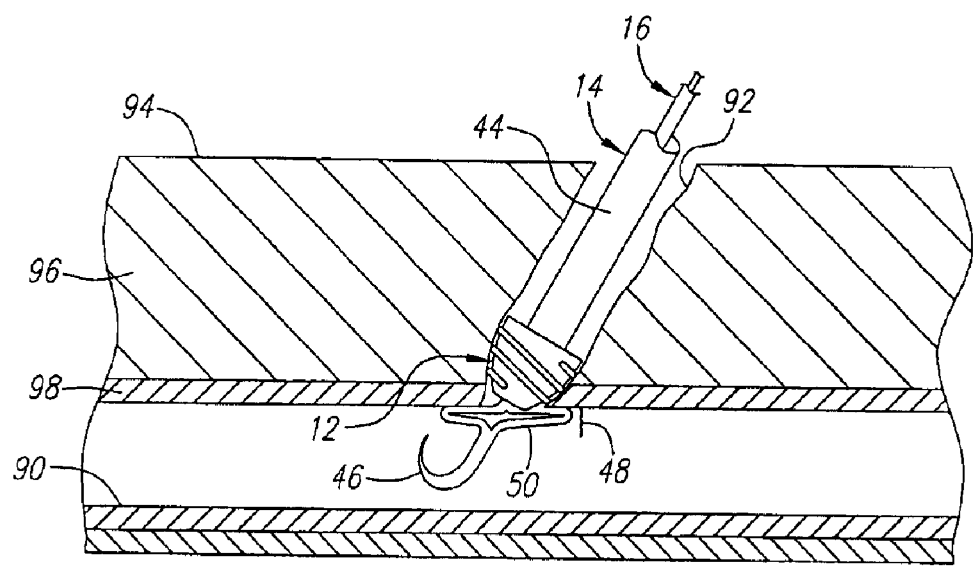

Turning to FIG. 8D, the wings 50 on the guide wire element 16 may be collapsed back to the collapsed configuration, e.g., by releasing the wings 53 on the actuator region 47 (not shown, see FIGS. 5A and 5B) or the handle 140 (also not shown, see FIGS. 6A and 6B). Once the wings 50 are collapsed, the guide wire element 16 may be withdrawn from the vessel 90.

Figure 8E:
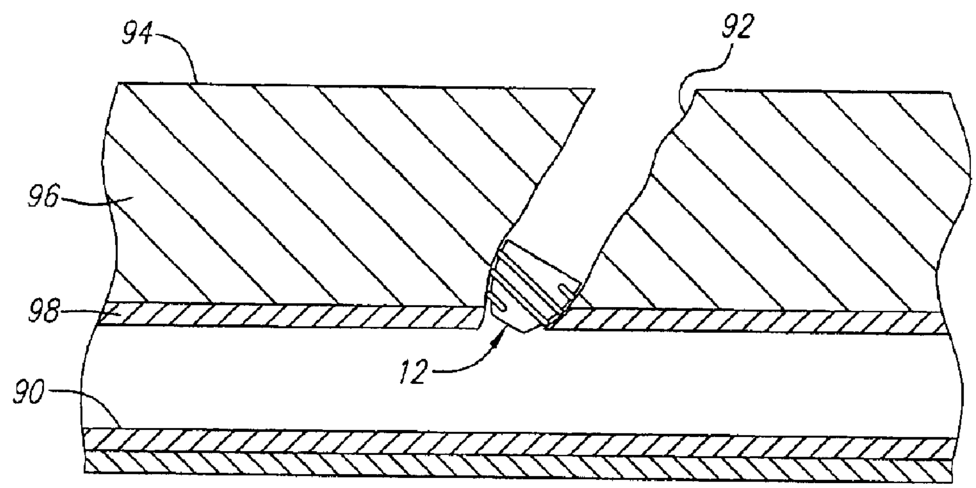

Turning to FIG. 8E, the plug member 12 may be deployed from the handle device 14, and the handle device 14 withdrawn from the passage 92. As explained above with respect to FIGS. 4A–4D, the handle device 14 may include inner and outer members 80, 70 that may be used to secure the plug member 12 to the handle device 14. When it is desired to deploy the plug member 12, the inner member 80 may be advanced distally relative to the outer member 70. This action may also compress the collet 60 located within the plug member 12, thereby substantially sealing the lumen 24 through the plug member 12. Finally, further advancement of the inner member 80 may advance the plug member off of the outer member 70, thereby releasing the plug member from the handle device 14.

Figure 9A:
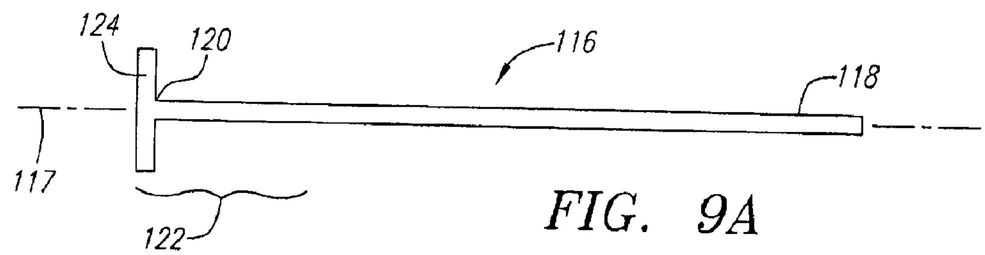
FIGS. 9A and 9B are side views of yet another embodiment of a guide wire element, in accordance with the present invention.
Figure 9B:
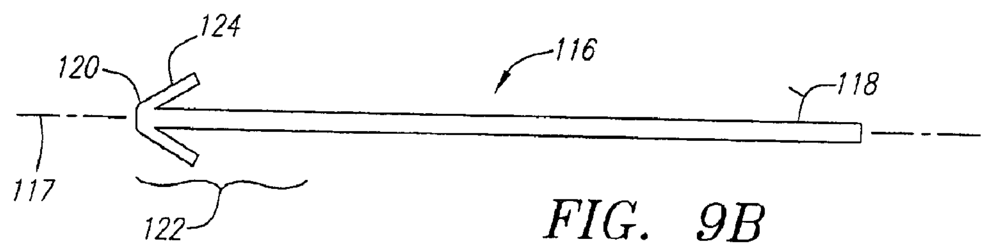

Turning to FIGS. 9A and 9B, another embodiment of a guide wire element 116 is shown that may be used with an apparatus to deliver a plug member 12 (not shown), in accordance with the present invention. The guide wire element 116 generally includes an elongated flexible or semi-rigid body defining a longitudinal axis 117 extending between a proximal end 118 and a distal end 120 thereof. Optionally, the guide wire element 116 may be tubular, e.g., including a bleed back lumen (not extending) extending between the proximal and distal ends 118, 120.

The guide wire element 116 may be formed from a biocompatible material, and preferably is formed at least partially from a bioabsorbable material, similar to the plug member 12 described above. More preferably, the guide wire element 116 includes a bioabsorbable distal portion 122 that may be detached from the remainder of the guide wire element 116. For example, the distal portion 122 may be severable from the remainder of the guide wire element 116. Alternatively, the guide wire element 116 may include cooperating connectors (not shown) that may be decoupled to release the distal portion 122.

The distal end 120 of the guide wire element 116 includes one or more lateral elements 124 that are biased to extend laterally, and preferably substantially perpendicular, with respect to the longitudinal axis 117, as shown in FIG. 9A. In the preferred embodiment shown, the lateral elements 124 are opposing legs or wings that extend away from one another. Alternatively, any number, e.g., one or more, of such legs or wings may be provided. The lateral elements 124 may be deflected to a collapsed configuration, as shown in FIG. 9B, e.g., to reduce a profile of the guide wire element 116 as it is advanced through a passage through tissue (not shown).

Figure 10A:
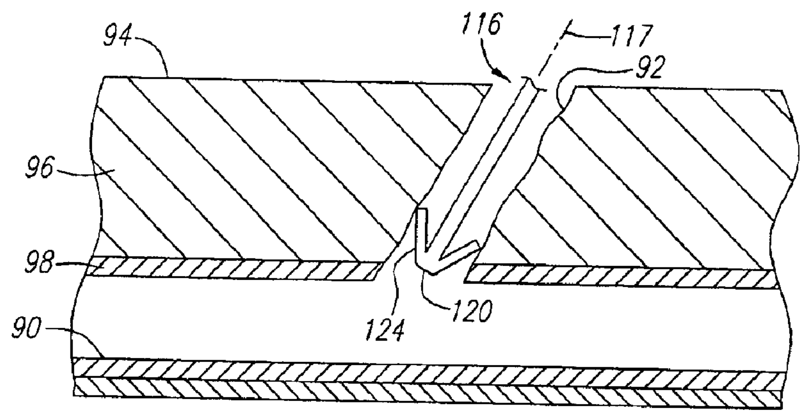
FIGS. 10A–10E are cross-sectional side views of a passage communicating with a blood vessel, showing a method for delivering a plug member into the passage using the guide wire element of FIGS. 9A and 9B.

Turning to FIGS. 10A–10E, a method for using the guide wire element 116 to facilitate delivering a plug member 12 is shown. Similar to the methods described above, a passage 92 may be formed during a procedure that extends through tissue 96, e.g., from a patient's skin 94 to a blood vessel 90. Before or after removing an introducer (not shown) positioned through the passage 92, the guide wire element 116 may be advanced through the passage 92 until the distal end 120 is positioned in the vessel 90. Because the lateral elements 124 are collapsible, as the guide wire element 116 is advanced within the passage 92, the lateral elements 124 may be deflected towards the collapsed configuration, as shown in FIG. 10A. If the guide wire element 116 includes a bleed back lumen, as the distal end 120 enters the vessel 90, blood may flow through the bleed back lumen, providing a visual indication that the vessel 90 has been reached.

Figure 10B:
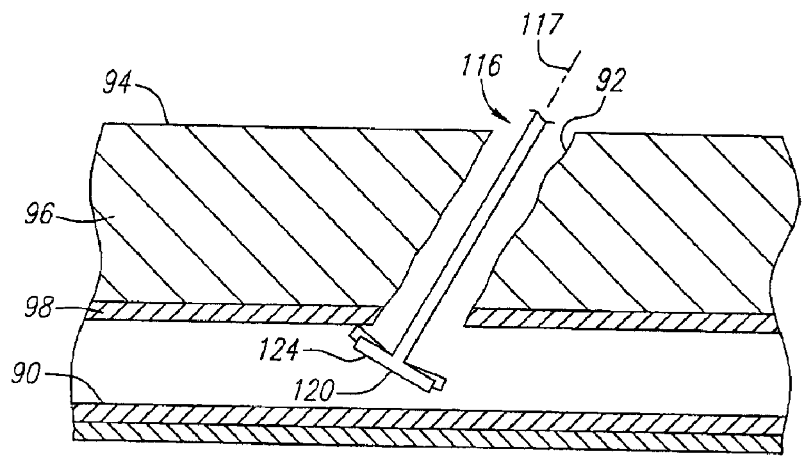

Turning to FIG. 10B, once the distal end 120 of the guide wire element 116 enters the vessel 90, the lateral elements 124 may resume their expanded configuration. The guide wire element 116 may then be withdrawn proximally until the lateral elements 124 contact a wall 98 of the vessel 90, thereby providing a tactile indication of the location of the vessel 90 relative to the patient's skin 94.

Figure 10C:
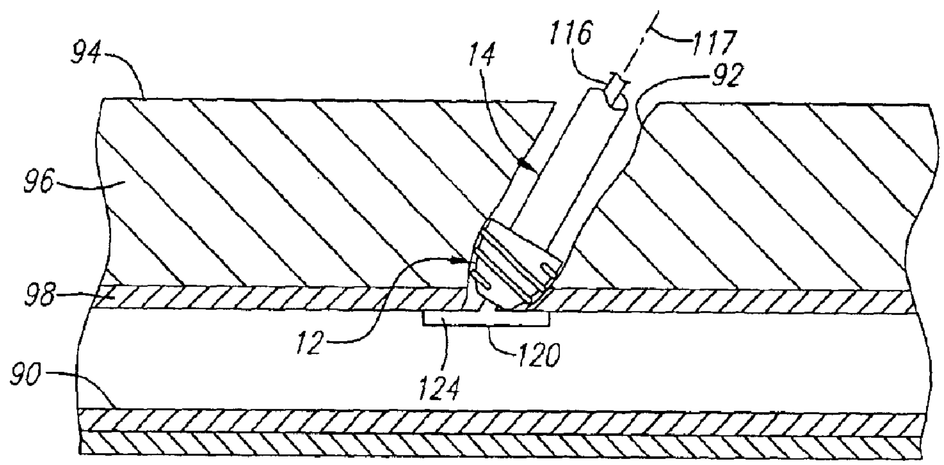

As shown in FIG. 10C, a handle device 14 carrying a plug member 12 may be advanced through the passage 92 over the guide wire element 116, similar to the previous embodiments. Optionally, the guide wire element 116 may include visual indicators, similar to the previous embodiments, to facilitate positioning of the plug member 12 relative to the wall 98 of the vessel 90. Optionally, similar to the previous embodiments, the plug member 12 and/or handle device 14 may include a bleed back lumen (not shown) for identifying when the plug member 12 has entered the vessel 90.

Once the plug member 12 is positioned at a desired location, the plug member 12 may be deployed from the handle device 14, similar to the previous embodiments. Unlike the previous embodiments, however, the distal portion 122 of the guide wire element 116 may remain within the lumen 24 of the plug member 12 as the plug member 12 is deployed. If the plug member 12 includes a collet or other sealing member 60, similar to that shown in FIGS. 4A–4D, the collet 60 may be compressed as the plug member 12 is deployed. Thus, as the collet 60 is compressed to substantially seal the lumen 24, it may engage the distal portion 122 of the guide wire element 116, thereby substantially anchoring the distal portion 122 of the guide wire element 116 to the plug member 12. In addition, if the guide wire element 116 includes a bleed back lumen, the collet 60 may compress the guide wire element 116 to substantially seal the bleed back lumen.

In addition, or alternatively, the plug member 12 may include flanges or other locking elements (not shown) that may slidably engage the guide wire element 116 as the plug member 12 is advanced over the guide wire element 116. If the plug member is directed proximally, the locking elements may engage the guide wire element 116 and prevent relative movement of the plug member 12 and guide wire element 116. Optionally, the guide wire element 116 may include ratchet elements (not shown) that may allow the locking elements to over the ratchet elements in a distal direction, but interlock to prevent movement in a proximal direction.

Figure 10D:
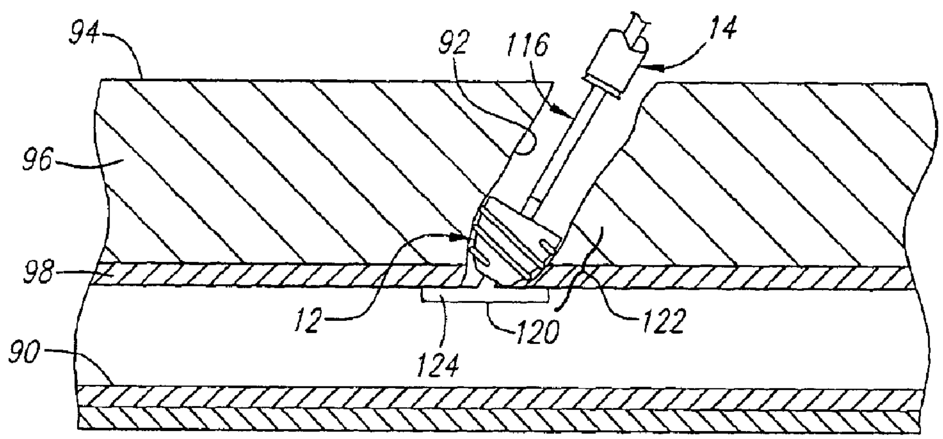

Turning to FIG. 10D, after the plug member 12 is released from the handle device 14, the handle device 14 may be withdrawn from the passage 92, leaving the plug member 12 and the guide wire element 116 within the body. Because the distal portion 122 of the guide wire element 116 is preferably formed from a bioabsorbable material, the distal portion 122 may be separated from the remainder of the guide wire element. For example, a cutting device (not shown) may be advanced into the passage 92 to sever the distal portion 122, whereupon the remainder of the guide wire element 116 may be withdrawn from the passage 92. Alternatively, if the guide wire element 116 includes cooperating connectors (not shown), the connectors may be decoupled to release the distal portion 122.

Figure 10E:
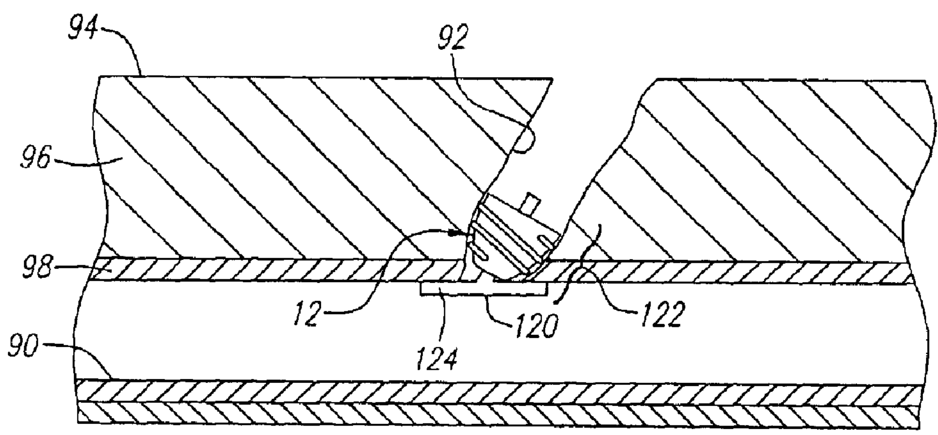

Thus, the plug member 12, as well as the distal portion 122 of the guide wire element 116 may remain within the passage 92. The plug member 12 may substantially seal and/or close the passage 92, as seen in FIG. 10E, and secure the distal portion 122 of the guide wire element 116 from separating from the plug member 12. As the tissue 96 surrounding the passage 92 heals, the distal end 318 of the guide wire element 316 and/or the plug member 12 may be absorbed by the body.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the spirit and scope of the appended claims.

What is claimed is:

1. A device for sealing a passage through tissue, comprising:

a generally annular body comprising a proximal end, a distal end, and a lumen extending between the proximal and distal ends, the lumen comprising a reduced cross-sectional region; and a generally annular sealing member slidably disposed within the lumen of the body, the sealing member comprising a lumen extending between proximal and distal ends thereof, and a plurality of shoulders disposed about the lumen of the sealing member, the shoulders being deflectable towards one another when the sealing member is moved at least partially into the reduced cross-sectional region, thereby at least partially sealing the lumen of the sealing member.

2. The device of claim 1, wherein the sealing member comprises a slot separating each adjacent shoulder.

3. The device of claim 1, wherein the body comprises a helical thread pattern on an outer surface extending at least partially between the proximal and distal ends.

4. The device of claim 1, wherein a distal opening of the lumen of the body is smaller than a proximal opening of the lumen of the body.

5. The device of claim 4, wherein the reduced cross-sectional region of the lumen of the body tapers distally towards the distal opening.

6. The device of claim 1, wherein the proximal end of the body comprises a substantially elliptical opening communicating with the lumen of the body.

7. The device of claim 1, wherein the sealing member comprises a material that is expandable when exposed to fluid to further seal the lumen of the sealing member.

8. The device of claim 1, wherein at least one of the body and the sealing member comprises bioabsorbable material.

9. The device of claim 8, wherein both the body and the sealing member comprise bioabsorbable material.

10. The device of claim 1, further comprising a handle device extending from the proximal end of the body, the body being detachable from the handle device.

11. The device of claim 10, wherein the handle device comprises an inner member at least partially received within the lumen of the body, the inner member being slidable for directing the sealing member into the reduced cross-sectional region.

12. The device of claim 11, wherein the handle device further comprises an outer member, the outer member comprising a distal end that engages the proximal end of the body for detachably coupling the body to the handle device.

13. An apparatus for sealing a passage through tissue, comprising:

a plug member comprising a generally annular body including a lumen extending between proximal and distal ends thereof, the lumen comprising a reduced cross-sectional region, and a generally annular sealing member slidably disposed within the lumen of the body, the sealing member comprising a plurality of shoulders disposed about a lumen of the sealing member, the shoulders being deflectable towards one another for at least partially sealing the lumen of the body; and a handle device comprising an outer member and an inner member including proximal and distal ends defining a longitudinal axis therebetween, the distal end of the outer member being detachably coupled to the proximal end of the body, the distal end of the inner member being slidable axially within the lumen of the body for at least partially moving the sealing member into the reduced cross-sectional region of the lumen in the body, thereby deflecting the shoulders towards one another to at least partially seal the lumen in the body.

14. The apparatus of claim 13, wherein the proximal end of the body comprises a proximal opening including a major axis and a minor axis, and wherein the outer member comprises opposing elements on the distal end that are movable away from one another to define a major axis that substantially engages the proximal opening to secure the body to the distal end of the outer member.

15. The apparatus of claim 14, wherein the inner member comprises one or more flared regions on its distal end, the inner member being movable proximally relative to the outer member, the one or more flared regions slidably engaging the opposing elements to move the opposing elements away from one another to engage the proximal opening in the body.

16. The apparatus of claim 15, wherein the inner member is movable distally relative to the outer member for disengaging the opposing elements on the outer member from the proximal end of the body.

17. The apparatus of claim 16, wherein the sealing member is at least partially directed into the reduced cross-sectional region of the lumen in the body as the inner member is moved distally, thereby deflecting the shoulders on the sealing member towards one another to at least partially seal the lumen in the body.

18. The apparatus of claim 14, the proximal opening in the body is substantially elliptical in shape, wherein the distal end of the first elongate member, and wherein the opposing elements on the outer member comprise opposing halves of the distal end of the outer member that are separated by slots.

19. The apparatus of claim 13, wherein the inner member comprises a lumen extending between its proximal and distal ends, the lumen communicating with the lumen in the body and being generally aligned with the lumen in the sealing member.

20. The apparatus of claim 19, further comprising a guide wire element comprising a proximal end receivable through the lumens in the inner member, the body, and the sealing member.

21. A method for sealing a passage through tissue from a patient's skin to a body lumen, comprising:

providing a guide wire element extending from the patient's skin through the passage and into the body lumen;

advancing a plug member into the passage over the guide wire element, the plug member comprising a lumen through which the guide wire element is inserted as the plug member is advanced into the passage, the plug member comprising a sealing member therein at least partially surrounding the guide wire element;

directing the sealing member into a reduced cross-sectional region of the lumen, thereby deflecting a plurality of shoulders on the sealing member towards one another to at least partially seal the lumen; and withdrawing at least a portion of the guide wire element from the passage.

22. The method of claim 21, wherein the plug member comprises an external thread pattern, and wherein the advancing step comprises rotating the plug member, thereby threading the plug member into the passage.

23. The method of claim 21, wherein the plug member is carried by the distal end of an elongate delivery device, the method further comprising releasing the plug member from the delivery device after the plug member is advanced into the passage.

24. The method of claim 23, wherein the sealing member is directed into a reduced cross-sectional region of the lumen as the plug member is released from the delivery device.

25. The method of claim 21, wherein the entire guide wire element is withdrawn from the passage before the sealing member is directed into the reduced cross-sectional region of the lumen.

* * * * *